(12) United States Patent
Berranger et al.

(10) Patent No.: US 8,158,807 B2
(45) Date of Patent: Apr. 17, 2012

(54) PROCESS FOR THE PREPARATION OF 6,6-DIMETHYL-3-AZABICYCLO-[3.1.0]-HEXANE COMPOUNDS UTILIZING BISULFITE INTERMEDIATE

(75) Inventors: Thierry Berranger, Baroeul (FR); Patrice Demonchaux, Cherewg (FR)

(73) Assignee: Schering Corporation, Kenilworth, NJ (US)

( * ) Notice: Subject to any disclaimer, the term of this patent is extended or adjusted under 35 U.S.C. 154(b) by 243 days.

(21) Appl. No.: 12/519,488

(22) PCT Filed: Dec. 18, 2007

(86) PCT No.: PCT/US2007/025809
§ 371 (c)(1),
(2), (4) Date: Dec. 3, 2009

(87) PCT Pub. No.: WO2008/082508
PCT Pub. Date: Jul. 10, 2008

(65) Prior Publication Data
US 2010/0145069 A1      Jun. 10, 2010

Related U.S. Application Data

(60) Provisional application No. 60/876,296, filed on Dec. 20, 2006.

(51) Int. Cl.
*C07D 209/52* (2006.01)
(52) U.S. Cl. ........................ 548/512; 548/515
(58) Field of Classification Search ........................ None
See application file for complete search history.

(56) References Cited

U.S. PATENT DOCUMENTS
2005/0059800 A1   3/2005   Sudhakar et al.

FOREIGN PATENT DOCUMENTS
| EP | 0004107 | 9/1979 |
|---|---|---|
| EP | 0008813 | 3/1980 |
| EP | 0010799 | 5/1980 |
| WO | WO 2007/075790 | 7/2007 |

OTHER PUBLICATIONS

Kollmeyer, et al. ACS Symposium Series: Synthesis and Chemistry of Agrochemicals, "Chemical Hybridizing Agents", Ch. 34, pp. 401-408 (Nov. 3, 1987).*
International Preliminary Report on Patentability which contains the full text of the Written Opinion on Patentability; as reported by the EPO on Jun. 22, 2006 available as an Internet publication on WIPO website; corresponding to PCT/EP2006/061409; 3 pages.

* cited by examiner

*Primary Examiner* — Yong Chu
*Assistant Examiner* — Michael Barker
(74) *Attorney, Agent, or Firm* — Sheldon O. Heber; Julie M. Lake

(57) ABSTRACT

The present invention provides for a process for preparing 6,6-Dimethyl-3-aza-bicyclo[3.1.0]hexane-2-sulfonate, an intermediate useful in the efficient preparation of (1R,2S,5S)-methyl 6,6-dimethyl-3-azabicyclo[3,1,0]hexane-2-carboxylic acid and esters and salts thereof, processes for preparing (1R,2S,5S)-methyl 6,6-dimethyl-3-azabicyclo[3,1,0]hexane-2-carboxylic acid and esters and salts thereof from the sulfonate intermediate and processes for preparing 6,6-Dimethyl-3-aza-bicyclo[3.1.0]hexane-2-sulfonate.

14 Claims, No Drawings

PROCESS FOR THE PREPARATION OF 6,6-DIMETHYL-3-AZABICYCLO-[3.1.0]-HEXANE COMPOUNDS UTILIZING BISULFITE INTERMEDIATE

CROSS-REFERENCE TO RELATED APPLICATIONS

This application is entered into national stage examination under 35 U.S.C. 371 and stems from International patent application No.: PCT/US2007/025809 filed in the U.S. PCT receiving office on Dec. 18, 2007, which claims the priority of U.S. provisional patent application Ser. No. 60/876,296 filed Dec. 20, 2006. Each of the aforementioned PCT and Provisional applications is incorporated by reference herein in its entirety.

FIELD OF THE INVENTION

The present invention relates to a process for preparing racemic methyl 6,6-dimethyl-3-azabicyclo[3.1.0]hexane-2-carboxylate (free base) from caronic acid. The invention relates also to the bisulfite adduct intermediate 6,6-dimethyl-3-azabicyclo[3.1.0]hexane-2-sodium sulfonate useful in preparing methyl 6,6-dimethyl-3-azabicyclo[3.1.0]hexane-2-carboxylate free base and the process for preparing the bisulfite adduct intermediate. The compounds obtained by these processes are useful as intermediates in the synthesis of compounds that have, for example, medicinal value.

BACKGROUND OF THE INVENTION

Identification of any publication in this section or any section of this application is not an admission that such publication is prior art to the present invention.

Esters of 6,6-dimethyl-3-azabicyclo[3.1.0]hexane-2-carboxylic acid are useful as intermediates in the synthesis of compounds that have utility, for example, as pharmaceuticals. For example, (1R,2S,5S)-6,6-dimethyl-3-azabicyclo[3.1.0]-hexane-2-carboxylic acid, methyl ester hydrochloride is disclosed in US Publication No. 2003-0216325 A1 which is incorporated herein by reference. This compound is a key intermediate used in preparation of the hepatitis C virus ("HCV") protease inhibitor having the following structure of formula Z:

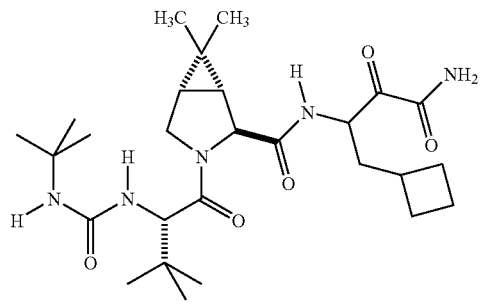

The compound of formula Z is useful for treating hepatitis C and related disorders. Specifically, the compound of formula Z is an inhibitor of the HCV NS3/NS4a serine protease.

Various methods are known in the art to make esters of 6,6-dimethyl-3-azabicyclo[3.1.0]hexane-2-carboxylic acid, which have the formula:

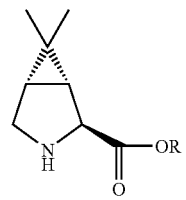

where R is, for example, alkyl, aryl, aralkyl, cycloalkyl and cycloalkylalkyl. For example, US Publication No. 2003-0216325 A1 discloses preparation of the compound of Formula 1:

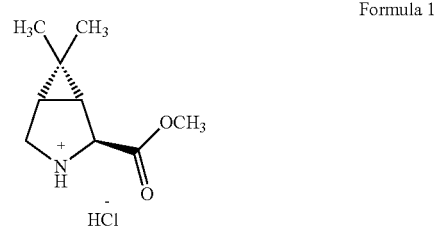

Formula 1 from the corresponding alcohol of Formula 2:

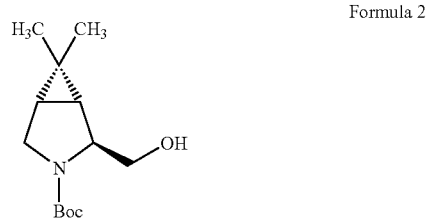

Formula 2 by performing a Jones oxidation and then cleaving the nitrogen protecting group with methanolic HCl. This procedure modifies the one disclosed by R. Zhang and J. S. Madalengoitia in *J. Org. Chem.*, 64, pp 330-31 (1999).

US Publication No. US 2005/0020689 A1, herein incorporated by reference, discloses a process for making 3-(amino)-3-cyclobutyl methyl-2-hydroxy-propionamide or a salt thereof, which is an intermediate in the synthesis of compound Z. This publication also claims some intermediates prepared in the synthesis.

US Publication No. US 2005/0059800, herein incorporated by reference, claims an alternative process for preparing the compound of formula Z, which involves using methyl 6,6-dimethyl-3-azabicyclo[3.1.0]hexane-2-carboxylic acid as a starting material.

US Publication No. US 2005/0059684 A1, herein incorporated by reference, prepares esters of 6,6-dimethyl-3-azabicyclo[3.1.0]hexane-2-carboxylic acid in a process summarized by Scheme 1

Scheme 1

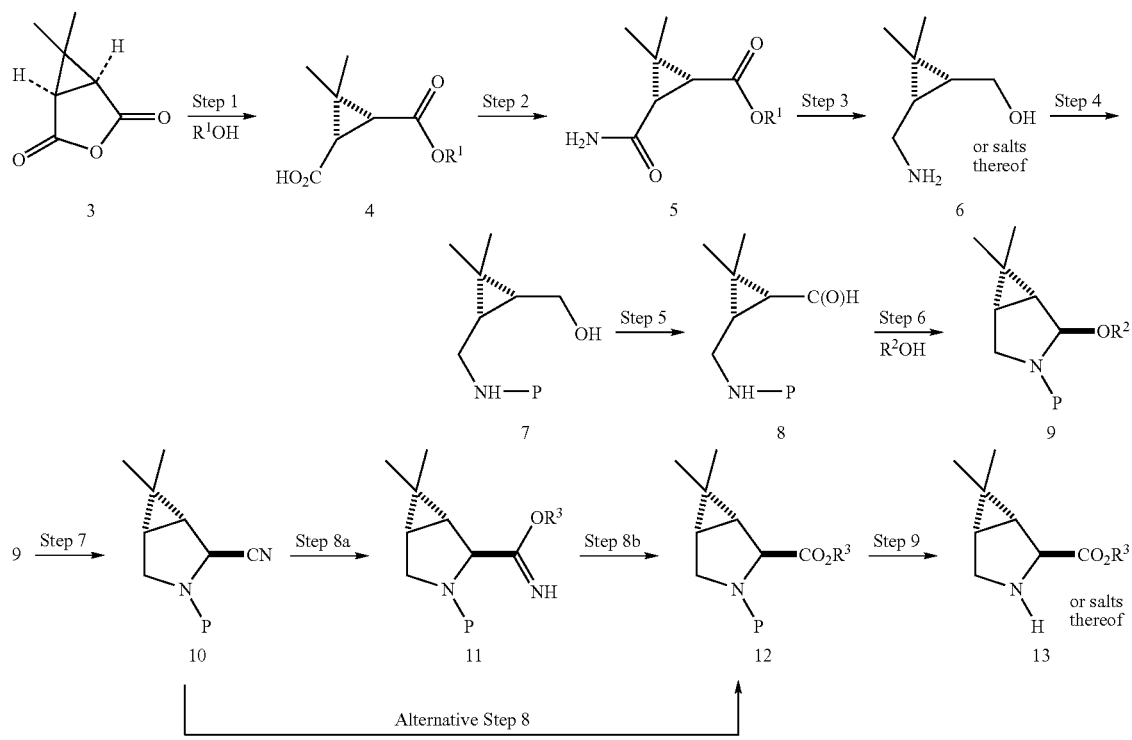

Alternative Step 8

EP 0 010 799 (the '799 publication) discloses a process for preparing acid compounds of the formula

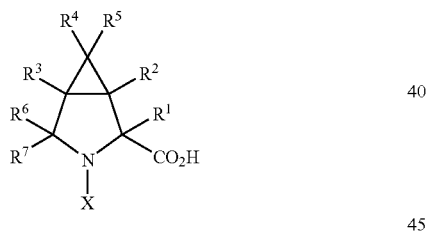

where $R^1$ is hydrogen or alkyl and $R^2$ to $R^7$ are, for example, alkyl, from the corresponding imine through a nitrile intermediate. Accordingly, the imine is reacted with a cyanating reagent to form the corresponding nitrile, which is subsequently hydrolyzed to form the acid derivative. The imine derivative is prepared by direct oxidation of a bicyclo-pyrrolidine compound of the formula

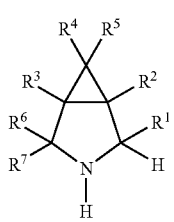

or by dehydrohalogenation of the corresponding halo-pyrrolidine derivative of the bicyclo-pyrrolidine. The document indicates that the cyanation step forming the nitrile generally leads exclusively to the formation of the trans geometric isomer and this stereochemistry is retained in the hydrolysis step.

U.S. Pat. No. 4,691,022 discloses a process for preparing an acid or ester derivatives of the formula where R is hydrogen or alkyl and $R^4$ and $R^5$, for example, may form a bicyclic ring system, from the corresponding nitrile. The process comprises converting, with an oxidizing agent in the presence of a silver salt, a pyrrolidine derivative into the corresponding $\Delta^1$-pyrrolidine derivative and subsequently reacting the pyrrolidine derivative with HCN, preferably generated by adding a metal cyanide in the presence of mineral acid to the reaction mixture, to form the nitrile. The product is prepared by subjecting the resulting nitrile to solvolysis. The patent does not disclose a process for making a particular isomer of these compounds in a high enantiomeric excess.

OBJECTIVES

In view of the foregoing, what is needed is a process for the provision, in high yield and high enantiomeric purity, of one particular enantiomer of the bicyclo-pyrrolidine compound used as an intermediate to HCV protease inhibitors compounds of Formula Z without the need for expensive, time consuming resolving methods, for example, chiral column chromatography. Moreover, what is needed is a process for the provision of intermediate compounds useful in the preparation of compounds of Formula Z which are amenable to commercial scale preparation of the intermediates in high enantiomeric purity. Accordingly, there remains a need for methods of providing intermediates useful in commercial scale synthesis of compounds useful in the treatment or prevention or amelioration of one or more symptoms of hepatitis C. These and other objectives and/or advantages are provided by the present invention.

SUMMARY OF THE INVENTION

In one aspect the present invention provides a process for making a racemic mixture of 6,6-dimethyl-3-azabicyclo[3.1.0]hexane-2-sodiumsulfonate adduct compounds of Formulae Va-S and Vb-S in predominantly trans-configuration. Compounds Va-S and Vb-S are useful intermediates in the preparation of the compound of Formula Z,

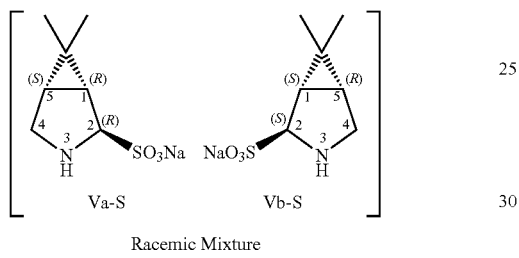

Racemic Mixture the process comprising reacting an imine mixture of compounds Formulae Va and Vb

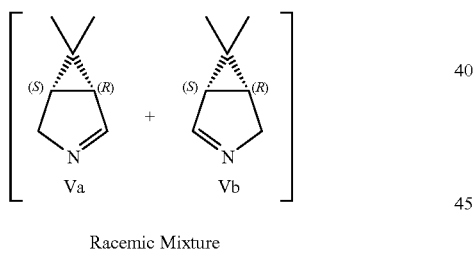

Racemic Mixture with sodium bisulfite under conditions promoting addition of the bisulfite moiety to the C-2 carbon in a trans-relationship to the C-6 carbon of the mixture of imine compounds of Formulae Va and Vb.

In some embodiments it is preferred to react the imine mixture of compounds of Formulae Va and Vb as an organic solution admixed with an aqueous bisulfite solution.

In some embodiments it is preferred to provide the imine (6,6-Dimethyl-3-aza-bicyclo[3.1.0]hex-2-ene) from which the sulfonate adduct is prepared by oxidizing the corresponding pyrrolidine (6,6-Dimethyl-3-aza-bicyclo[3.1.0]hexane) compound. In some embodiments it is preferred to carry out oxidation of the pyrrolidine compound mixture utilizing a potassium persulfate and silver nitrate.

Another aspect of the invention is the provision of a mixture of the compounds of Formulae VIa, that is, (1R,2S,5S)-6,6-dimethyl-3-azabicyclo[3.1.0]hexane-2-nitrile and VIb, that is (1S,2R,5R)-6,6-dimethyl-3-azabicyclo[3.1.0]hexane-2-nitrile, by the process comprising:

(i) reacting caronic anhydride with benzylamine under conditions favorable to form the 2,4 dione of Formula IIb

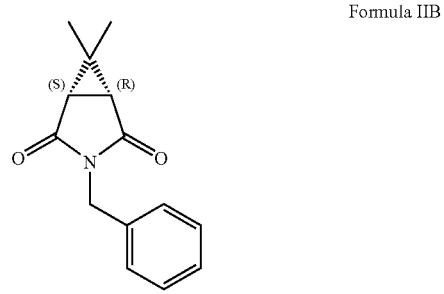

(ii) reducing the dione of Formula IIB to the 3-aza-benzyl-bicyclohexane compound of Formula IIC;

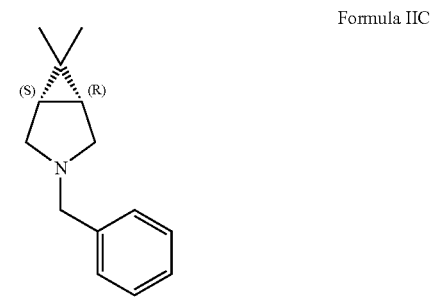

(iii) reducing the compound of Formula IIC to 6,6-Dimethyl-3-aza-bicyclo[3.1.0]hexane;

(iv) oxidizing the hexane product from reducing Step (iii) to provide the mixture comprising the imines of Formulae Va and Vb;

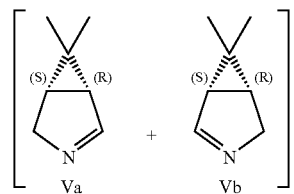

(v) reacting the mixture of compounds produced in oxidizing step (iv) with sodium bisulfite under conditions to provide the trans-bisulfite adduct compounds of Formula Va-S and Vb-S;

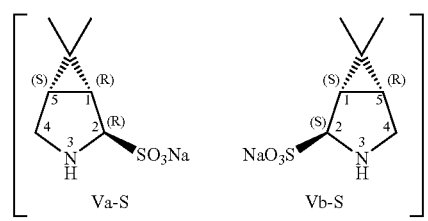

(vi) reacting the mixture of bisulfite adduct compounds produced in Step (v) with a cyanide source to form the corresponding mixture of the nitrite compounds of Formula VIa and VIb;

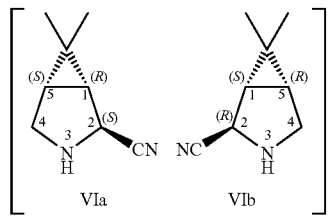

(vii) optionally hydrolyzing the racemic mixture of nitrile compounds formed in Step (vi) in the presence of an alcohol of the Formula R—OH to provide the corresponding mixture of alkyl ester compounds of Formula I and Ia

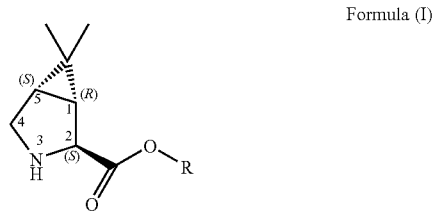

where R is alkyl, substituted alkyl, aryl, substituted aryl, aralkyl, substituted aralkyl, cycloalkyl or substituted cycloalkyl; and (viii) optionally treating a solution of the mixture of ester compounds formed Step (vii) with a chiral tartaric acid derivative to precipitate the tartaric acid derivative salt, in high enantiomeric excess, of either the compound of Formula I or the compound of Formula Ia from said solution of the mixture. In some embodiments it is preferred to carry out Step (ii), the dione reducing step, by treating the dione with a metal hydride, preferably lithium aluminum hydride, Red-Al®, and borane, more preferably lithium aluminum hydride. In some embodiments it is preferred to reduce the compound of Formula IIC in Step (iii) by hydrogenating the compound in a metal-mediated hydrogenolysis, preferably using Pd/carbon and hydrogen. In some embodiments it is preferred in Step (iv) to oxidize the reduced compound from Step (iii) to an imine by reacting the pyrrolidine produced in Step (iii) with an oxidizer comprising sodium persulfate and silver nitrate. In some embodiments it is preferred to form an imine by converting the pyrrolidine produced in Step (iii) to a haloamine and subsequently dehydrohalogenating the haloamine to an imine, for example, by the sodium hypochlorite or N-chloro succinamide processes described in a U.S. provisional application No. 61/004,601 filed on Nov. 28, 2007.

In some embodiments, in Step (v), the bisulfite reacting step, it is preferred to react the imine mixture of compounds of Formulae Va and Vb as an organic solution admixed with an aqueous bisulfite solution. In some embodiments, is Step (vi), the cyano-adduct step, it is preferred to use sodium cyanide as a source of cyanide from which the cyano adduct is prepared. In some embodiments utilizing optional hydrolysis step (vii), it is preferred to carry out the hydrolysis using HCl and methanol.

In some embodiments utilizing optional precipitation Step (viii) it is preferred to precipitate the desired enantiomer of Formula I with a chiral tartaric acid derivative selected from di-p-toluoyl-D-tartaric acid ("D-DTTA") and dibenzoyl-D-tartaric acid ("D-DBTA") thus precipitating a salt of the (1R, 2S,5S)-methyl 6,6-dimethyl-3-azabicyclo-[3.1.0]hexane-2-carboxylate enantiomer. In some embodiments utilizing optional precipitation Step (viii) it is preferred to precipitate the undesired enantiomer of Formula Ia in a high enantiomeric excess by treating the solution with a chiral tartaric acid derivative selected from l-di-p-toluoyl-L-tartaric acid ("L-DTTA") and l-dibenzoyl-L-tartaric acid salt ("L-DBTA"), thus precipitating a tartaric acid derivative salt of (1S,2R,5R)-methyl 6,6-dimethyl-3-azabicyclo[3.1.0]hexane-2-carboxylate, and isolate the desired salt from the supernatant solution after filtering out the precipitate salt of the undesired enantiomer.

Another aspect of the present invention the provision of the intermediate compounds of Formula Va-S and Vb-S.

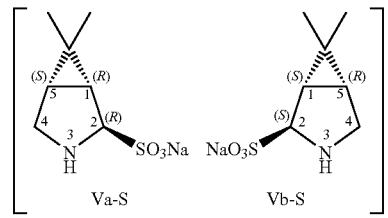

DESCRIPTION OF THE INVENTION

As used above, and throughout the specification, the following terms, unless otherwise indicated, shall be understood to have the following meanings:

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl, groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, and alkoxy. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent, such as those defined above. Suitable, non-limiting examples include: H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl carbon atom. Preferred acyl groups contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups is as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-$S(O_2)$— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

Enantiomeric excess ("e.e.") is a percentage expressing the extent to which one enantiomer (e.g., R-enantiomer) is produced over the other (e.g. S-enantiomer), calculated by subtracting the difference in the amount of each enantiomer produced divided by the sum of the amount of each enantiomer produced.

In one embodiment, the present invention provides a sulfonate adduct of an intermediate compound in accordance with Scheme 2, which is useful in the process for preparing compounds of Formula Z. Preparation of a corresponding sulfonate adduct from 6,6-dimethyl-3-azabicyclo[3.1.0]-hexane is presented schematically in Steps 1 and 2 of Scheme 2.

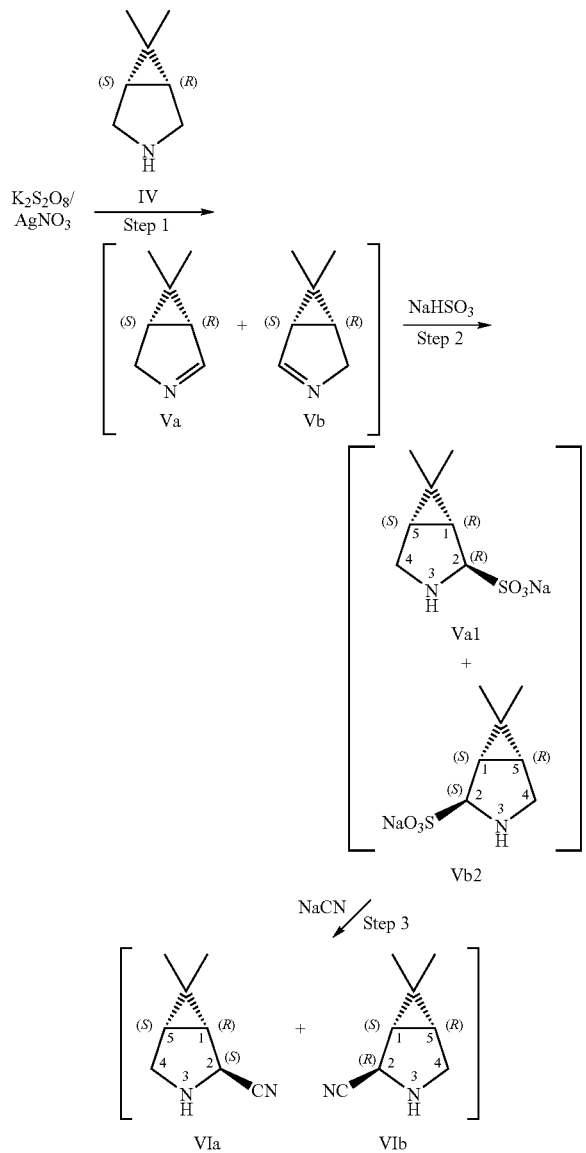

Sulfonate intermediates prepared in accordance with Scheme 2, Step 2, are useful in the preparation of the nitrile intermediates, the use of which in the preparation of compounds of Formula Z has been described in earlier applications and in copending application No. 60/876,447, which is incorporated by reference herein. In some embodiments the nitrile intermediates will be converted to an ester in accordance with Steps 4 and 5 of Scheme 3. In some embodiments the desired enantiomer, (1R,2S,5S) 6,6-dimethyl-3-azabicyclo[3.1.0]-hexane-2-alkylester, the compound of Formula SI, will be isolated as the salt of that ester in accordance with Step 5 of Scheme 3.

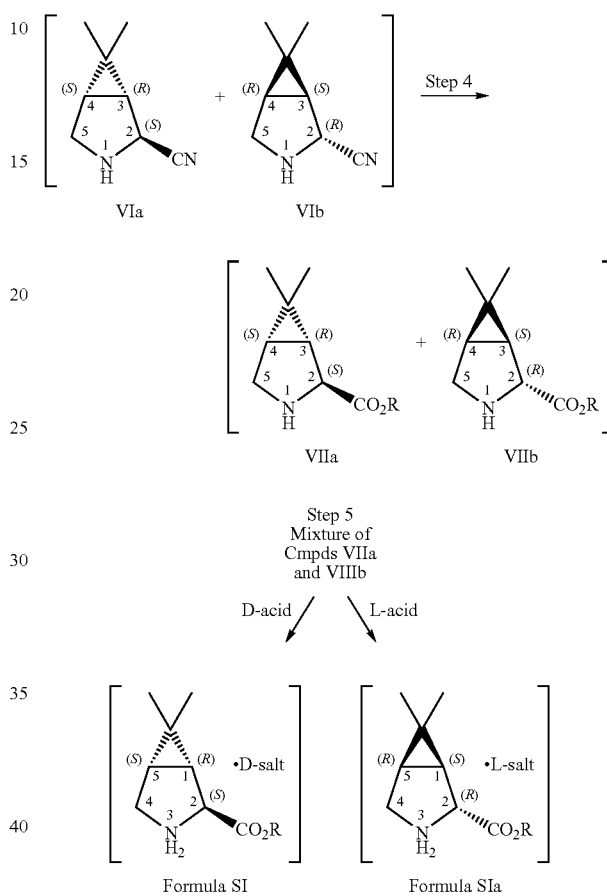

wherein R is an alkyl, substituted alkyl, aryl, substituted aryl, aralkyl substituted aralkyl, cycloalkyl, or substituted cycloalkyl group, D-acid is selected from di-p-toluoyl-D-tartaric acid (D-DTTA) and dibenzoyl-D-tartaric acid (D-DBTA); D-salt is the anion corresponding to the D-acid selected, that is, either di-p-toluoyl-D-tartarate or dibenzoyl-D-tartarate; L-acid is selected from di-p-toluoyl-L-tartaric acid (L-DTTA) and dibenzoyl-L-tartaric acid (L-DBTA); and L-salt is the anion corresponding to the L-acid selected, that is, either di-p-toluoyl-L-tartarate or dibenzoyl-L-tartarate. In some embodiments the desired ester will be precipitated and isolated by filtration. In some embodiments the undesirable ester will be precipitate using an L-acid, and the desired ester will be isolated from the supernatant after filtering out the unwanted ester precipitate.

Processes for making the starting pyrrolidine, 6,6-dimethyl-3-azabicyclo[3.1.0]-hexane (the compound of Formula IV) from caronic anhydride are known, and described in the above-mentioned patents and patent applications, all of which are incorporated herein by reference. Some of these processes are summarized schematically in Scheme 4.

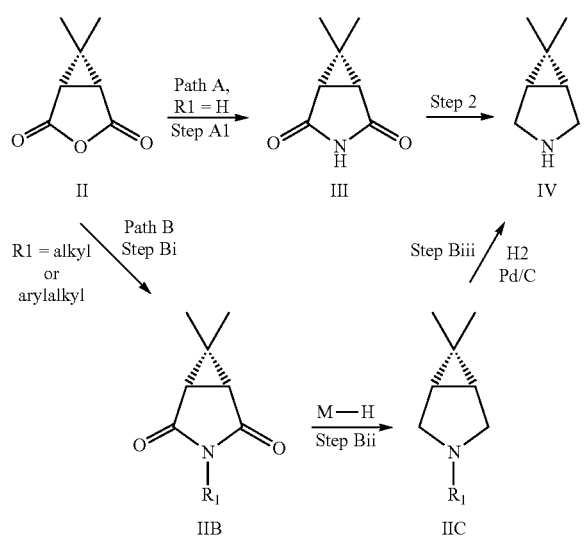

Methods to prepare caronic anhydride (the compound of Formula II) are known in the art. The compound of Formula II may be prepared, for example, from the synthesis disclosed in US Publication No. 2005/0059648 A1, which in Example 1 therein details a method for preparing the anhydride from ethyl chrysanthemumate in accordance with published procedures.

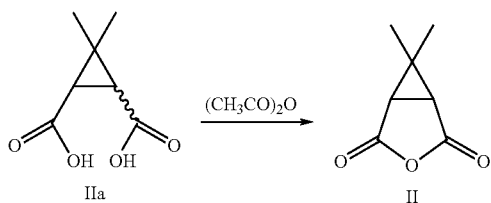

For example, as shown in Scheme 5, racemic 3,3 dimethylcyclopropane-1,2-dicarboxylicacid (IIa) is dissolved/suspended in a reaction solvent and treated with acetic anhydride in the presence of sulfuric acid forms racemic caronic anhydride (Formula II). The caronic anhydride prepared in this reaction may be isolated for use in any of the processes shown in Scheme 4.

Procedure A:

Caronic anhydride (Formula II) can be catalytically converted to the compound of Formula III in a suitable solvent to yield the imide of Formula III. In a subsequent step the imide is reduced to the pyrrolidine compound of Formula IV for use as described herein. In some embodiments of the invention it is preferred to employ solvents selected from water, tetrahydrofuran, methanol, isopropanol, methyl isobutyl ketone, xylenes, and formamide. Suitable catalysts for carrying out this conversion include, for example, 4-N,N-dimethylaminopyridine (DMAP) and lutidine. The catalyst is employed in the presence of a nitrogen source. Suitable nitrogen source reagents include, but are not limited to, $NH_3$, $NH_4OH$, $H_2NC(O)NH_2$, $H_2NC(O)H$, $NH_4O_2CH$, and $NH_4O_2CCH_3$. In some embodiments it is preferred to carry out the reaction at a temperature of from about 10° C. to about 200° C.

Procedure B (Two-Steps),

A second method for the provision of the compound of Formula IV from caronic anhydride (Formula II) is a three-step sequence to yield the imide of Formula IIC which is reduced to the compound of Formula IV.

Step Bi:

An intermediate dione of Formula IIB is prepared from caronic anhydride by reaction with a reagent selected from an aralkyl, substituted aralkyl or alkenyl amine in the presence of a solvent. In some embodiments of the invention it is preferred to employ amines selected from $ArylCH_2NH_2$ and $AllylNH_2$. In some embodiments of the invention it is preferred to use a solvent selected from t-butyl methylether (TBME), tetrahydrofuran, methanol, toluene, xylene and mixtures of two or more thereof. In some embodiments of the invention it is preferred to carry out the reaction at a temperature of from about 0° C. to about 200° C.

Step Bii:

The intermediate dione of formula IIB can be converted to the pyrrolidine compound IIC by reduction of the carbonyl groups in a suitable solvent with a metal hydride, for example, sodium borohydride and lithium aluminum hydride. In some embodiments it is preferred to carry out this reduction using a reagent selected from lithium aluminum hydride ("LiAlH$_4$"), sodium bis(2-methoxyethoxy)aluminum dihydride ("Red-Al®"), and borane. In some embodiments of the invention it is preferred to carry out the reduction reaction in a solvent selected from tetrahydrofuran, 2-methyl tetrahydrofuran, tert-butyl methyl ether, 1,2-dimethoxyethane, toluene and mixtures of two or more thereof. In some embodiments it is preferred to isolate the product by distilling off the solvent. In some embodiments of the invention it is preferred to carry out the reduction reaction at a temperatures of from about −20° C. to about 80° C.

Step Bii:

The intermediate compound of Formula IIC can be reduced to the compound of Formula IV using metal-mediated hydrogenolysis reaction conditions. In some embodiments it is preferred to use a catalyst comprising palladium on carbon (Pd/C) in the presence of hydrogen gas. One example of suitable reaction conditions can be found in the following reference: R. C. Bernotas and R. V. Cube, *Synthetic Communication*, 1990, 20, 1209.

Optionally, the compound of Formula IV may be converted to the corresponding salt by treating it with an acid to aid in isolation of the compound. Suitable acids include, but are not limited to, mineral acids, for example, HCl, HBr, HI, $HNO_3$ or $H_2SO_4$. In some embodiments it is preferred to use a suitable organic solvent to provide a mineral acid solution for this treatment, for example, alcohol solvents, for example methanol and isopropanol.

Each of the steps presented in Scheme 2 are discussed next in detail.

Step 1—Oxidation to Form the Imine Compounds of Formula Va and Vb:

The pyrrolidine ring in the bicyclo-compound compound of Formula IV is oxidized to yield the corresponding imine. Since the multiple bond introduced into the pyrrolidine ring can be introduced in either of two locations on the ring, this step yields a mixture of isomer compounds of Formulae Va and Vb.

In some embodiments it is preferred to carry out the oxidation by treating the compound of Formula IV with sodium or potassium peroxodisulfate and a catalytic amount of silver nitrate as a catalyst, preferably from about 0.01 to about 0.10 molar equivalents of silver nitrate. In these embodiments it preferred to use a solvent comprising water or a water/solvent mixture, for example water mixed with a solvent selected from acetonitrile and mixtures thereof.

In some embodiments it is preferred to employ potassium peroxodisulfate with silver nitrate in the presence of an alkali-metal cyanide, preferably potassium cyanide. In some embodiments utilizing this oxidation method it is preferred to employ water as the reaction medium and suspend the pyrrolidine substrate undergoing oxidation therein. Moreover, it is preferred to provide a reaction mixture containing water, potassium persulfate and silver nitrate, and to add the compound of Formula IV to the reaction mixture. In some embodiments using potassium peroxodisulfate/silver nitrate oxidation in Step 1, it is preferred to employ a catalytic amount of silver nitrate, for example from about 2 mole % to about 10 mole %, more preferably from about 5 to about 7.5 mole % compared to the amount of substrate present. In some embodiments it is preferred to employ at least about 1.1 equivalent of potassium peroxodisulfate based on the amount of pyrrolidine substrate to be oxidized along with from about 2.3 equivalents to about 3.0 equivalents of sodium hydroxide dissolved in about 10 volumes to about 15 volumes water. In some embodiments employing the peroxodisulfate/silver nitrate oxidation procedure, it is preferred to use at least 2 equivalents of an alkali metal cyanide, preferably potassium cyanide, in the reaction mixture. In some embodiments employing peroxodisulfate oxidation in Step 1, it is preferred to carry out the reaction at a temperature of from about $-5°$ C. to about $+5°$ C., more preferably from about $-5°$ C. to about $0°$ C. In some embodiments using potassium peroxodisulfate oxidation in Step 3, it is preferred to work up the reaction by quenching with sodium thiosulfate aqueous solution and extract the product into methyl tertiary butyl ether (MTBE), concentrate the extract and replace the MTBE with methanol by adding methanol to the solution and distilling off the MTBE. In some embodiments utilizing this work up it is preferred to employ the methanolic solution of the product imine provided by the work up directly in subsequent steps of the inventive process.

In some embodiments it is preferred to form an imine by converting a pyrrolidine, for example, the compound of Formula IV or of Formula IIC (described herein) to a haloamine and subsequently dehydrohalogenating the haloamine to an imine. Examples of processes utilizing this process, for example, preparing a chloramine by halogenating a pyrrolidine using sodium hypochlorite or N-chloro succinamide are described in a U.S. provisional application No. 61/004,601 filed on Nov. 28, 2007, which is incorporated by reference herein in its entirety.

Step 2—Conversion of Imine to Sulfonate Adduct

The mixture of imines of Formula Va and Vb are converted to the corresponding sulfonate adduct compounds of Formulae Va1 and Vb2 by treating the mixture of compounds with a source of sodium bisulfite. It is preferred to prepare the source of sodium bisulfite by dissolving in sodium metabisulfite in water. In some embodiments it is preferred to use a weight of sodium metabisulfite which provides a solution that is from about 1 equivalent to about 1.5 equivalents of sodium metabisulfite. In some embodiments it is preferred to employ a solution that is about 10 wt. % sodium metabisulfite. It is preferred to perform the reaction by contacting the aqueous sodium bisulfite source with an organic solution of the mixture of compounds of Formulae Va and Vb, preferably a solution comprising from about 8 wt. % of the mixture of compounds to about 32 wt. % of the mixture of compounds in methyl-tertiarybutyl ether (MTBE), more preferably about 16 wt % of the mixture of compounds of Formulae Va and Vb in MTBE. The reaction can be carried across the phases by agitating the immiscible organic and aqueous solutions while preferably maintaining the temperature from about $20°$ C. to about $35°$ C., more preferably from about $20°$ C. to about $25°$ C. It is preferred to utilize the 6,6-dimethyl-3-azabicyclo [3.1.0]-hexane-2-sulfonate sodium formed in the aqueous portion of the reaction mixture in situ without isolation after separating the organic and aqueous layers of the reaction mixture. Surprisingly, this adduct is formed under mild conditions with predominantly trans-addition of the sulfonate adduct to the C-2 position of the azacyclohexene compounds of Formula Va and Vb Step 3—Cyano-Group Functionalization of 2-Sulfonate Adducts of Formula Va1 and Va2 and Step 4—Hydrolysis of Resulting 2-Cyano-Group:

In Step 3 of Scheme 2, the mixture of sulfonate adduct compounds of Formulae Va1 and Vb2 are converted to the corresponding nitrile compounds of Formulae VIa and VIb by treatment with a cyanide source. The addition of the cyano group occurs at carbon 2, with preferential attack on the opposite face of the imine ring from which the methylene group forming the cyclopropyl ring of the bicyclo compound projects. Accordingly, the addition of cyano-group preferentially forms one of the two enantiomers, with reference to Scheme 2, shown in brackets as compounds VIa and VIb. Preferably this reaction is carried out by treating the aqueous solution of bisulfite adduct prepared in Step 2 with solid sodium cyanide. Preferably the reaction temperature is maintained at a temperature of less than about $25°$ C., more preferably in a range of from about $20°$ C. to about $25°$ C. In some embodiments it is preferred to extract the nitrile compounds from the aqueous medium in which they were prepared into an organic solvent, preferably MTBE, by stirring the aqueous reaction mixture with a similar volume of MTBE. In some embodiments it is preferred to convert the nitrile compounds extracted into the MTBE solution in this step in accordance with process steps 4 and 5 presented above in Scheme 3, without isolation of the compounds provided therefrom from the MTBE solution.

Accordingly, in some embodiments, with reference to Step 4 of Scheme 3, following extraction of the nitrile compounds, a solvolysis is performed in situ on the MTBE solution of compounds of Formulae VIa and VIb to the corresponding ester compounds VIIa and VIIb. Preferably the solvolysis is carried out by adding an alcohol, ROH, wherein R is defined above, in the presence of a molar excess of a mineral acid, for example, HCl, followed by treatment with a molar excess of base, for example, sodium bicarbonate or ammonia, to neutralize the excess acid. Preferably R in R—OH is selected from methyl and t-butyl. Preferably, the mineral acid is HCl and is provided by passing HCl gas into the alcohol reaction solvent, followed by treatment with a molar excess of base, for example, sodium bicarbonate or ammonia, to neutralize the excess acid. In some embodiments it is preferred to carry out the solvolysis reaction at a temperature of from about $-30°$ C. to about $25°$ C., more preferably the solvolysis is carried out at a temperature of about $-10°$ C. or less.

In some embodiments using methanol, after the desired amount of HCl has been bubbled into the reaction mixture, the reaction mixture is warmed to room temperature to complete the methanolysis reaction, thus providing the compounds of Formulae VIIIa and VIIb as the methyl ester. In some embodiments using this workup it is preferred to carry out the completion of the methanolysis at an elevated temperature, for example, from about $50°$ C. to about $60°$ C. In some embodiments using this work up, after the methanolysis reaction is complete, it is preferred to concentrate the reaction mixture to a slurry, dilute the slurry with from about 4 volumes to about 8 volumes of MTBE and about 4 volumes of water, cool the mixture to a temperature of from about −5° C. to about +5° C., and add to the cold mixture about 0.2 equivalents of potassium phosphate tribasic dissolved in two additional volumes of water.

In some embodiments using this work up procedure it is preferred to adjust the pH with aqueous base to a pH of from about pH 9 to about pH 9.5 while maintaining the temperature of the mixture at from about 0° C. to about +5° C. In some embodiments using this work up, it is preferred to separate out the MTBE layer, wash it, and concentrate it to a volume of from about ½ to about ⅓ the volume, and replace the MTBE in the concentrate with methanol by distilling off the MTBE after the addition of methanol. In some embodiments using this work up, the resulting methanol solution containing the Formula VII racemate is utilized in Step 6.

Step 5—Enantiomeric Salt Formation:

With reference to Step 5 of Scheme 3, the formation of a selected enantiomer salt is accomplished by adding to the mixture of compounds of Formulae VIIa and VIIb either: (a) D-DTTA (di-p-toluoyl-D-tartaric acid) or D-DBTA (dibenzoyl-D-tartaric acid) to precipitate the (1R,2S,5S) enantiomer; or (b) L-DTTA (di-p-toluoyl-L-tartaric acid) or L-DBTA (dibenzoyl-L-tartaric acid) to precipitate the (1S,2R,5R) enantiomer shown. Each of these chiral acids are commercially available reagents. As mentioned above, D-DTTA reacts with the (1R,2S,5S) enantiomer present in the mixture of compounds of Formulae VIIa and VIIb and L-DTTA with the (1S,2R,5R) enantiomer present in the mixture of compounds of Formulae VIIa and VIIb, precipitating the corresponding di-p-toluoyl-tartaric acid salt in at least about 90% enantiomeric excess. Similarly, D-DBTA reacts with the (1R,2S,5S) enantiomer present in the mixture of compounds of Formulae VIIa and VIIb and L-DTTA with the (1S,2R,5R) enantiomer present in the mixture of compounds of Formulae VIIa and VIIb, precipitating the corresponding dibenzoyl-tartaric acid salt in at least about 85% enantiomeric excess. In some embodiments it is preferred to employ solvents in this step selected from methanol, TBME and mixtures thereof. When mixed solvents are used it is preferred to use a ratio of TBME:MeOH of from about 2:1 to about 4:1. In some embodiments of the invention it is preferred to carry out the precipitation reaction at a temperatures of from about 15° C. and about 50° C.

In some embodiments of the present invention process, the enantiomer salt precipitated in Step 5, for example, the salt of Formulae SI and SIa, for example, a DTTA salt of formula SI, is converted to an HCl salt in accordance with the following process, for subsequent use in the synthesis of HCV protease inhibitor compounds. In some embodiments the isolated enantiomeric salt is suspended in a mixture of isopropyl alcohol and MTBE, preferably in a volumetric ratio of i-propanol:MTBE of from about 1:7 to about 1:8. This suspension is treated with from about 1.18 to about 1.20 equivalents of hydrochloric acid in an isopropanol solution (based on the amount of salt used), preferably having a concentration of 5M or less. In some embodiments using the optional HCl salt conversion step, when the conversion has proceeded to completion the reaction mixture is cooled to insure that the hydrochloride salt has precipitated. When precipation has completed, the precipitate is isolated by filtration and vacuum dried.

The following non-limiting EXAMPLES are provided to illustrate further the present invention. It will be apparent to those skilled in the art that many modifications, variations and alterations to the present disclosure, both to materials, methods and reaction conditions, may be practiced. All such modifications, variations, and alterations are intended to be within the spirit and scope of the present invention.

EXAMPLES

Unless otherwise stated, all solvents and reagents are articles of commerce, and used as received. Unless otherwise stated, the following abbreviations have the stated meanings in the Examples below:
mL=milliliters
g=grams
eq=equivalents
THF=tetrahydrofuran
MeOH=methanol
Me=methyl
TBME=methyl tert-butyl ether
ACN=acetonitrile
Ph=phenyl Example 1

Preparation of 6,6-Dimethyl-3-N-benzyl-aza-bicyclo[3.1.0]hexane-2,4-dione (IIB)

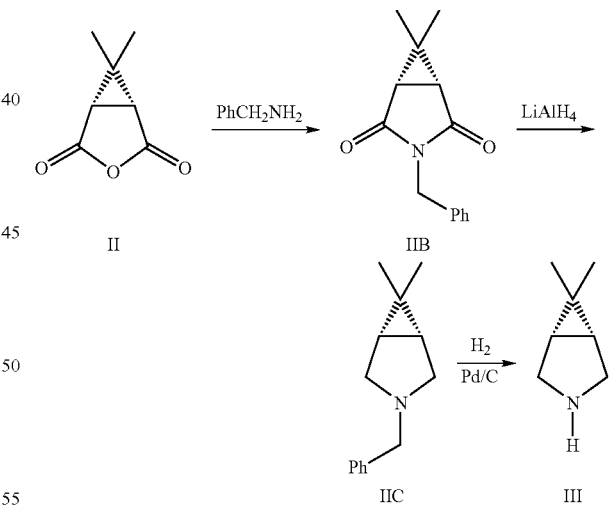

Step 1: IIB from I

To a flask were charged 51.32 g of compound II (0.37 mol, 1 eq.) and 50 mL TBME. While stirring, the mixture was cooled to between 0 and 10° C. 40.0 mL of benzylamine (39.24 g, 0.37 mol, 1 eq) was added dropwise over approximately 30 minutes. After the addition was complete, the TBME was removed by distillation at between 60 and 70° C. and the mixture was gradually heated to an internal temperature between 170 and 180° C. The solution was maintained between 170 and 180° C. for approximately 3 to 5 hours to complete the cyclization. The resulting solution was cooled to between 60 and 70° C., and 100 mL of a solution of 5% water in isopropanol was added and the mixture was cooled to room temperature. After cooling further to between 0 and 10° C., the product was isolated by filtration, rinsed with clean, cold isopropanol, and dried in a vacuum oven to afford 70.99 g of the benzyl imide, IIB, (85%). $^1$H NMR (CDCl$_3$) δ7.39 (m, 2H); 7.28 (m, 3H); 4.53 (s, 2H); 2.31 (s, 2H); 1.20 (s, 3H); 1.01 (s, 3H).

Step 2—IIC from IIB

In Step 2, the benzyl imide (IIb) is reduced using LiAlH$_4$ to provide the corresponding pyrrolidine in accordance with the following procedure. LiAlH$_4$ (2.4 M in THF, 1.3 mol) was placed in a round bottom flask equipped with a temperature probe, condenser and mechanical stirrer. The mixture was warmed and held at 50° C. To another round bottom flask equipped with a mechanical stirrer was added imide (compound IIB, 229 g, 1.0 mol) and THF (750 mL). The resulting mixture was agitated 5 min. and added to LiAlH$_4$ solution via addition funnel at a rate that allowed a gentle reflux of THF. The addition funnel was rinsed with THF (50 mL) and added to the mixture. The resultant suspension was held at reflux 2 h. The mixture was allowed to cool to room temperature. To an additional large round bottom flask equipped with a mechanical stirrer was added Potassium Sodium tartrate tetrahydrate (734 g, 2.6 mol), water (1.4 L) and NaOH (208 g, 5.2 mol). The solution was stirred at 20° C. 15 min. To the aqueous solution was charged the imide suspension slowly over 1 h 30 min. The resulting biphasic mixture was heated to 40-45° C. and agitated 15 min. The mixture was allowed to settle for 15 min. at 40-45° C. The organic was separated from the aqueous layer. The aqueous was extracted with MTBE (460 mL). The combined organic phase was concentrated in vacuo to give the benzylated amine (IIC, 191 g, 95%) as an orange oil.

Step 3—III from IIC

To a round bottom flask was charged benzylated amine (179.5 g, 0.89 mol), MeOH (360 mL) and charcoal (5 g). The suspension was filtered and the cake washed with additional MeOH (50 mL). To the filtrate was added acetic acid (90 mL) and the solution charged to a Buchi hydrogenator. To an additional flask was added 5% Pd/C (17.9 g, 10% w/w) and MeOH (30 mL). The mixture was added to the hydrogenator. The hydrogenator was charged with H$_2$ (3×3 bar) and the resultant suspension agitated at 20-25° C. for 6 h. The catalyst was filtered and the hydrogenator washed with MeOH (2×100 mL). The combined solvents were concentrated in vacuo at 40° C. until the solution became viscous. To the solution was added water (120 mL) and the resultant mixture cooled to 20° C. To this mixture was added 10 N NaOH (180 mL) and MTBE (450 mL). The biphasic mixture was agitated 10 min. and allowed to settle an additional 10 min. The organic phase was heated to 90° C. and concentrated at atmosphere. The resultant crude residue was distilled at 130 mm Hg to give the compound of Formula III (72.8 g, 97.8%) as a colorless liquid.

Example 2

Preparation of 6,6-dimethyl-3-aza-bicyclo[3.1.0]hex-2-ene (V)

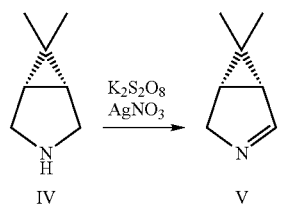

To a flask were charged 41.4 g of NaOH (1.04 mol, 2.3 eq.) and 134 g of K$_2$S$_2$O$_8$, 750 mL of water and 100 mL of acetonitrile at −5° C. 50 g of compound IV (0.45 mol, 1.0 eq) were added and the reaction mixture was again cooled to −5° C. Over 1-2 hours while maintaining the reaction temperature between −5 and 0° C. 20 mL of aqueous AgNO$_3$ (3.9 g, 0.0225 mol, 0.05 eq) were added to the reaction mixture. The reaction mixture was warmed to 0 to 2° C. and the reaction was allowed to proceed to completion. Upon completion, the mixture was warmed to room temperature and diluted with 360 mL TBME. The layers were separated, and the aqueous layer was extracted with TBME. The combined organic layers were dried over anhydrous Na$_2$SO$_4$ and filtered. The solution was purified by fractional distillation to yield V as a colorless oil which solidified upon standing to form a white crystalline solid compound V, (65-75% yield). $^1$H NMR (CDCl$_3$) δ 7.30 (t, J=2.2 Hz, 1H), 3.80 (ddd, J=6.8, 1.4, 0.6 Hz, 1H), 3.49 (dd, J=4.7, 2.8 Hz, 1H), 2.06 (dd, J=6.0, 1.7 Hz, 1H), 1.61 (dd, J=6.6, 1.8 Hz, 1H), 1.03 (s, 3H), 0.68 (s, 3H).

Example 3

Step 2, Scheme 2—Preparation of Sulfonate Adduct Compounds of Formulae Va1 and Va2

Into a 1 L round bottom flask was placed 300 mL of water at ambient temperature and 34.2 g of sodium metabisulfite (article of commerce, used as received). The reaction mixture was stirred for 10 minutes at ambient to insure a homogeneous solution. To the bisulfite solution was added, over 1 hours, 208 g of the imine compound of Formula V in the form of the MTBE solution prepared in accordance with Example 2, Procedure B while maintaining the reaction mixture temperature at less than 35° C. The addition funnel was rinsed with an additional 10 mL of MTBE which was added to the reaction mixture and the combined reaction mixture was stirred for one hour while maintaining the reaction mixture at ambient temperature. After 1 hour the organic and aqueous phases of the reaction mixture were separated. The aqueous phase was washed with 50 mL of MTBE.

Example 4

Step 3, Scheme 2—Preparation of Nitrile Compounds of Formulae VIa and VIb

The entire amount of the aqueous phase prepared in Example 3 was placed in a 1 L round bottom flask. To the flask was added, over a 10 minute period, 17.6 g of sodium cyanide (article of commerce, used as received) at a rate that maintained the temperature of the reaction mixture at less than 25°

C. The reaction mixture was stirred for 1 hour while maintaining the temperature of the mixture between 20° C. and 25° C. At the end of 1 hour, 130 mL of MTBE was added all at once to the reaction mixture and stirred for 5 minutes while maintaining ambient temperature. The organic and aqueous layers were separated. The organic layer was washed with two 33 mL aliquots of 20 wt/% aqueous NaCl solution and used in Example 5.

Example 5

Step 4, Scheme 3—Preparation of Ester Compounds of Formulae VIIa and VIIb

Into a 1 L round bottom flask was placed 168 g of HCl as a 28 wt. % methanol solution. The entire amount of MTBE solution containing the nitrile prepared in Example 4 was added to the methanolic HCl over a 45 minute period while maintaining the reaction mixture at a temperature of 30° C. or less. After the addition, the reaction mixture was heated to reflux (approximately 50° C.) and refluxed for 5 hours. After 5 hours a partial vacuum was applied to the reaction flask and MTBE/Methanol/HCl mixture was distilled off without exceeding 50° C. in the reaction mixture until a paste was obtained. To the warm paste was added all at once 130 mL of MTBE, thereby providing a suspension. The suspension was cooled to a temperature of between 0° C. and 5° C. To the suspension was added 130 mL of water with stirring until a clear biphasic mixture was obtained. Over a 10 minute period the entire amount of a solution made from 13.8 g tripotassium phosphate monohydrate in 66 mL of water was added to the reaction mixture while maintaining the temperature at less than 5° C. The pH of the reaction mixture was adjusted to a pH of 9.3 by adding 36 mL of 10N NaOH aqueous solution. The reaction mixture was agitated for an additional 15 minutes while maintaining the temperature between 0° C. and 5° C. Agitation was discontinued and the layers separated. The aqueous layer was extracted with 66 mL of MTBE which was added to the organic layer. The combined organic phases containing the ester compounds of Formula VIIa and VIIb were washed with a 66 mL aliquot of 20% brine solution and retained. HPLC yield calculated 75% based on amount of starting nitrile.

Example 6

Step 5, Scheme 3—Precipitation of D-Salt Ester Compound of Formula SI

Into a 1 L round bottom flask was charged 175 mL of methanol and 69.5 g of D-DTTA, with heating to 50° C. to obtain a solution. Over a one hour period, into the flask was added the entire amount of MTBE solution prepared in Example 5 containing 175.0 g of the mixture of compounds of Formulae VIIa and VIIb. The addition funnel used to add the solution was rinsed with 10 mL MTBE which was added to the reaction mixture. The reaction mixture was agitated for 3 hours while being heated to reflux (approximately 50° C. to 55° C.). The reaction mixture was cooled to 40° C. and the precipitate was isolated by filtration. The solids were washed with three 60 mL aliquots of methanol at 40° C., and dried at 40° C. under atmosphere to obtain 58.6 g of the DTTA salt. Calculated yield was 50% based on the amount of methyl ester used. Enantiomeric excess of (1R,2S,5S) enantiomer was 97.5%.

While the present invention has been described with and in conjunction with the specific embodiments set forth above, these examples are meant to be illustrative and not limiting. Many alternatives, modifications and other variations thereof will be apparent to those of ordinary skill in the art. All such alternatives, modifications and variations are intended to fall within the spirit and scope of the present invention.

What is claimed is:

1. A process for preparing a mixture of 6,6-dimethyl-3-azabicyclo[3,1.0]hexane-2-sulfonatesodium adduct compounds of Formulae Va-S and Vb-S,

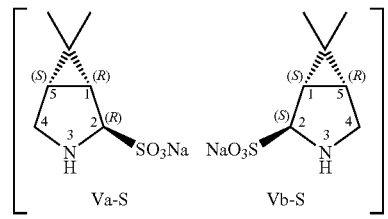

the process comprising reacting an organic solution of a imine mixture of compounds Formulae Va and Vb

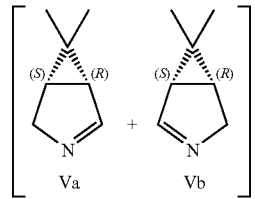

with a source of sodium bisulfite.

2. The process of claim 1 wherein, the organic solution of imine comprises methyl tertiary butyl ether, the source of sodium bisulfite is an aqueous solution of sodium bisulfite and the reaction is carried out by admixing the organic and aqueous solutions.

3. The process of claim 1 wherein the sodium bisulfite source is an aqueous solution comprising water and sodium metabisulfite.

4. The process of claim 3 further comprising providing an imine for the reaction by a process comprising oxidizing the pyrrolide compound of Formula IVa:

wherein "R" is selected from H, alkyl and alkyl-aryl.

5. The process of claim 4 wherein "R" is H and said pyrrolidine compound is oxidized utilizing a reagent comprising potassium persulfonate and silver nitrate and the oxidation is carried out by adding the pyrrolidine compound into a MTBE/water solution containing at least one equivalent of potassium persulfate and from about 0.01 to about 0.10 equivalents of silver nitrate.

6. A process for the provision of a mixture of nitrile compounds of Formulae VIa and VIb,

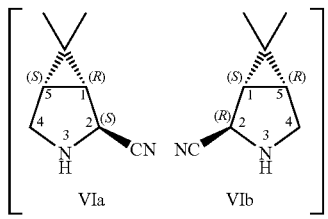

the process comprising:
(i) reacting caronic anhydride with benzylamine to form the 2,4 dione of formula IIb Formula IIB

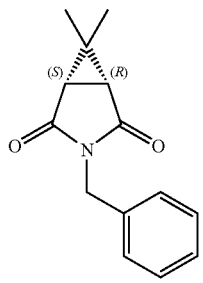

(ii) reducing the dione of Formula IIB to the 3-aza-benzyl-bicyclohexane compound of Formula IIC;

Formula IIC

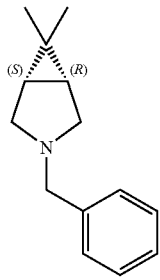

(iii) reducing the compound of Formula IIC to 6,6-Dimethyl-3-aza-bicyclo[3.1.0]hexane;
(iv) oxidizing the hexane product from reducing Step (iii) to provide a mixture comprising the imines of Formulae Va and Vb:

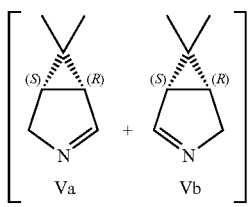

(v) reacting the mixture of compounds produced in oxidizing step (iv) with sodium bisulfite to provide the trans-bisulfite adduct compounds of Formula Va-S and Vb-S;

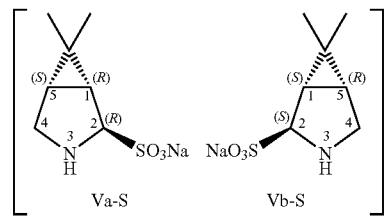

(vi) reacting the mixture of bisulfite adduct compounds produced in Step (v) with a source of cyano adduct to form the corresponding mixture of the nitrile compounds of Formula VIa and VIb.

7. The process of claim 6 wherein said dione reducing Step (ii) is carried out by reacting the dione with LiAlH$_4$ and wherein Step (iii) reduction of said compound of Formula IIC is carried out by hydrogenation mediated with a Pd/C catalyst.

8. The process of claim 7 wherein said oxidizing Step (iv) is carried out by a process comprising treating the 6,6-Dimethyl-3-aza-bicyclo[3.1.0]hexane formed in Step (iii) with an oxidizing reagent comprising postassium persulfate and a silver nitrate catalyst.

9. The process of claim 6, which further includes the step of hydrolyzing the mixture of nitrile compounds of Formula VIa and VIb formed in Step (vi) by treatment with a mineral acid in the presence of an alcohol of the Formula R—OH to provide the corresponding mixture of alkyl ester compounds of Formula I and Ia

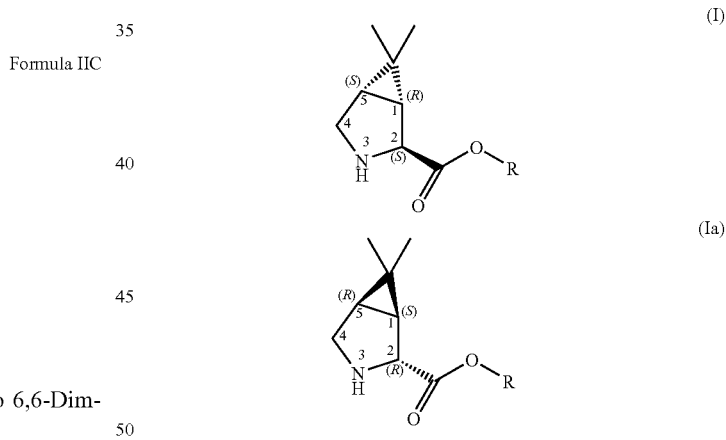

where R is alkyl, substituted alkyl, aryl, substituted aryl, aralkyl, substituted aralkyl, cycloalkyl or substituted cycloalkyl.

10. The process of claim 9, further including the step of treating a solution of the mixture of ester compounds of Formula I and Ia with a chiral tartaric acid derivative to precipitate, in high enantiomeric excess, the tartaric acid derivative salt of either the compound of Formula I or the compound of Formula Ia from said solution of the mixture.

11. The process of claim 10 wherein the tartaric acid derivative is selected from di-p-toluoyi-D-tartaric acid ("D-DTTA") and dibenzoyl-D-tartaric acid ("D-DBTA") thereby precipitating a salt of the (1R, 2S, 5S)-methyl 6,6-dimethyl-3-azabicyclo-[3.1.0]hexane-2-carboxylate enantiomer.

12. The process of claim 10 wherein the tartaric acid derivative is selected from I-di-p-toluoyl-L-tartaric acid ("L-

DTTA") and I-dibenzoyl-L-tartaric acid salt ("L-DBTA"), thereby precipitating a salt of the (1S, 2R, 5R)-methyl 6,6-dimethyl-3-azabicyclo[3.1.0]hexane-2-carboxylate enantiomer.
13. The compound of Formula Va-S
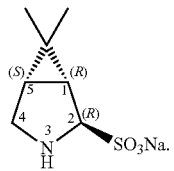
Va-S
14. The Compound of Formula Vb-S
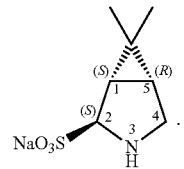
Vb-S
* * * * *